United States Patent [19]
Boyd et al.

[11] Patent Number: 5,014,293
[45] Date of Patent: May 7, 1991

[54] COMPUTERIZED TOMOGRAPHIC X-RAY SCANNER SYSTEM AND GANTRY ASSEMBLY

[75] Inventors: Douglas P. Boyd, San Francisco, Calif.; Giovanni Lanzara, Rome, Italy

[73] Assignee: Imatron, Inc., South San Francisco, Calif.

[21] Appl. No.: 416,921

[22] Filed: Oct. 4, 1989

[51] Int. Cl.⁵ .................. A61B 6/00; A61B 6/02; H05G 1/02
[52] U.S. Cl. ........................ 378/197; 378/11; 378/22; 378/39; 378/196; 378/4
[58] Field of Search ............... 378/4, 39, 193, 22, 378/196, 11, 21, 55, 197, 198

[56] References Cited

U.S. PATENT DOCUMENTS

| | | | |
|---|---|---|---|
| 3,617,749 | 11/1971 | Massiot et al. | 378/197 |
| 4,200,799 | 4/1980 | Saito | 378/197 |
| 4,481,656 | 11/1984 | Janssen et al. | 378/196 |
| 4,802,197 | 1/1989 | Juergens | 378/197 |

FOREIGN PATENT DOCUMENTS 2220559  11/1973  Netherlands ............ 378/196

Primary Examiner—Edward P. Westin
Assistant Examiner—Don Wong
Attorney, Agent, or Firm—Flehr, Hohbach, Test, Albritton & Herbert

[57] ABSTRACT

A scanner assembly having a C-shaped gantry rotatably supported by a support head. An x-ray source and a detector assembly are mounted on said gantry for independent movement with respect to one another along said gantry.

4 Claims, 6 Drawing Sheets

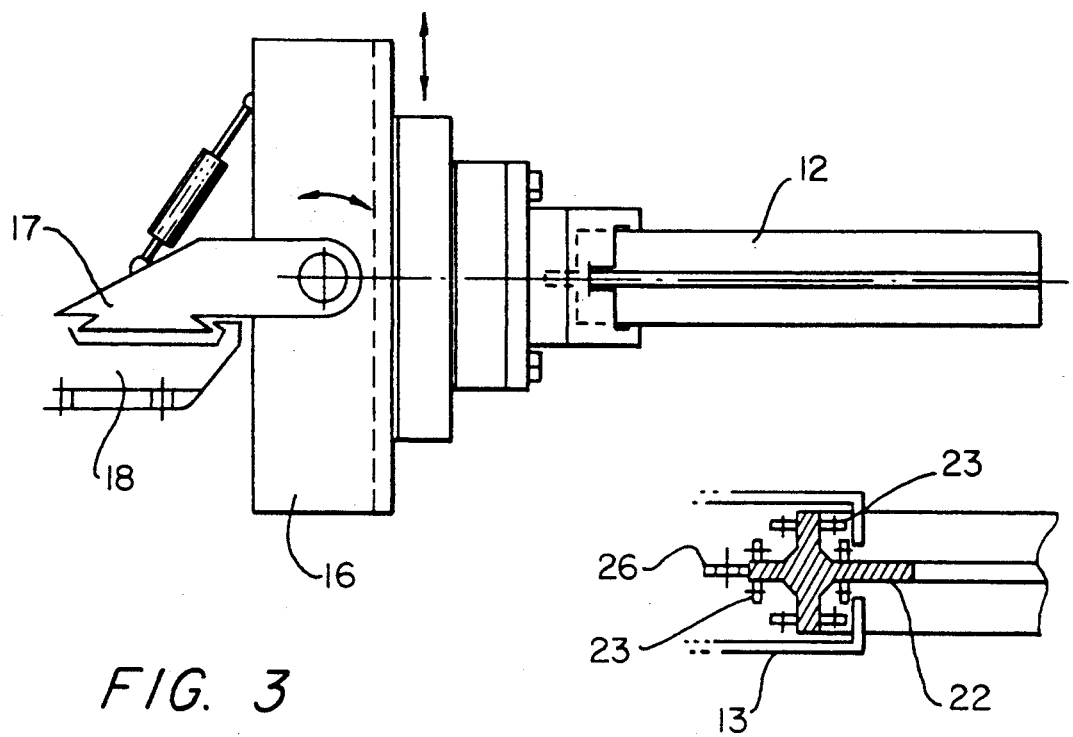
FIG. 3
FIG. 4
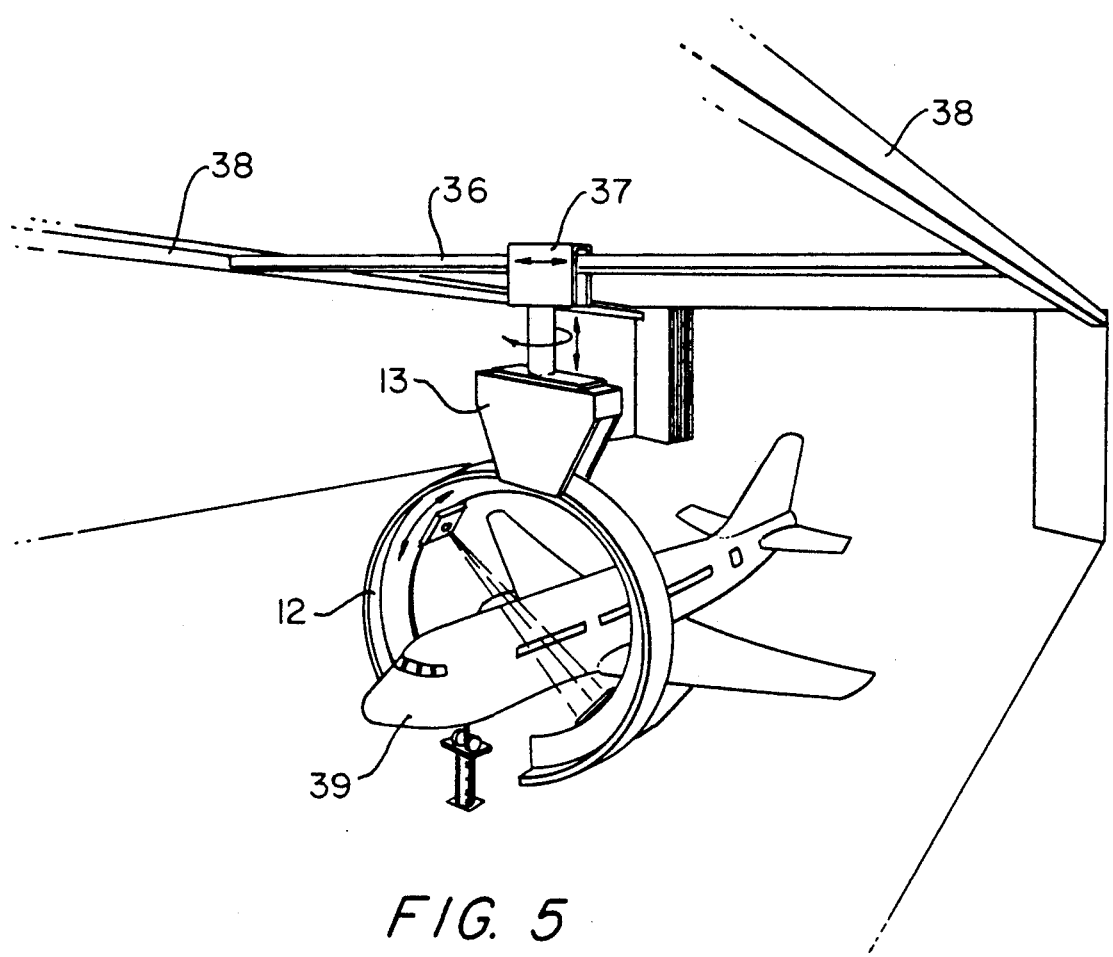
FIG. 5

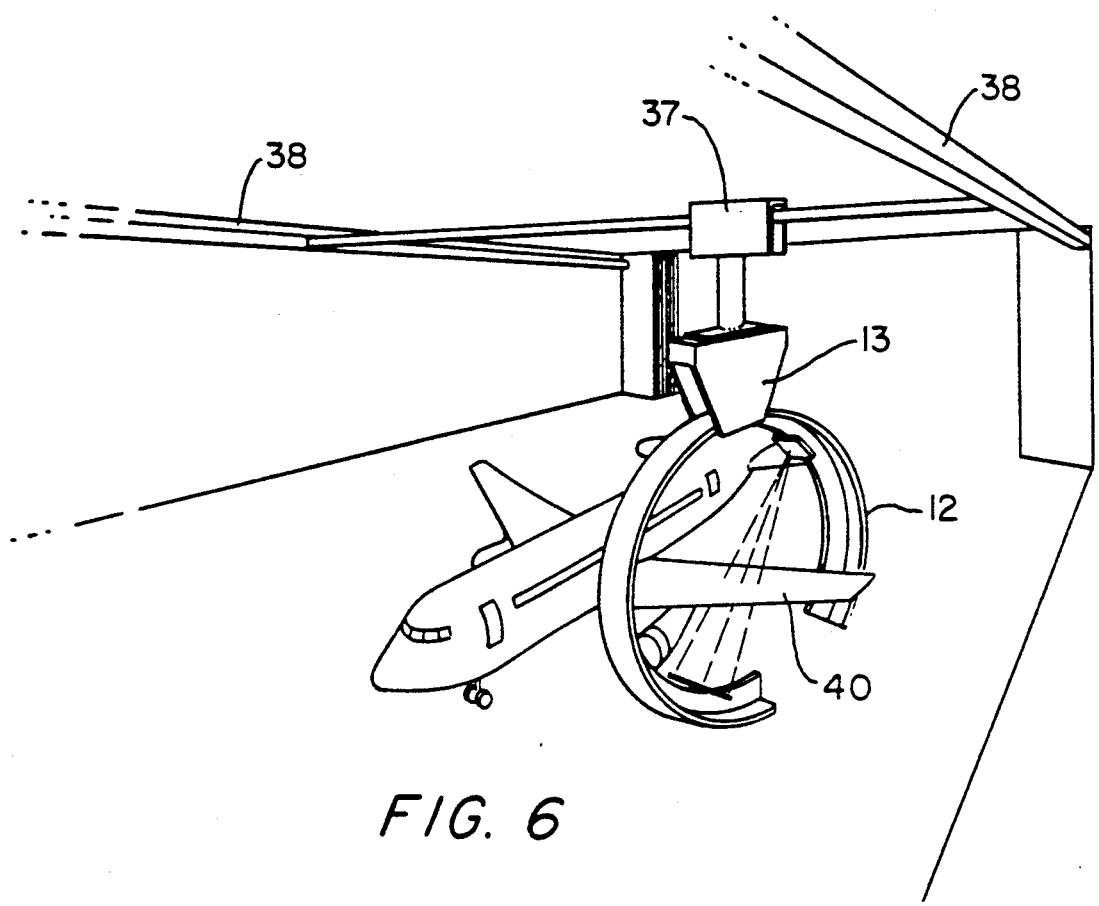
FIG. 6
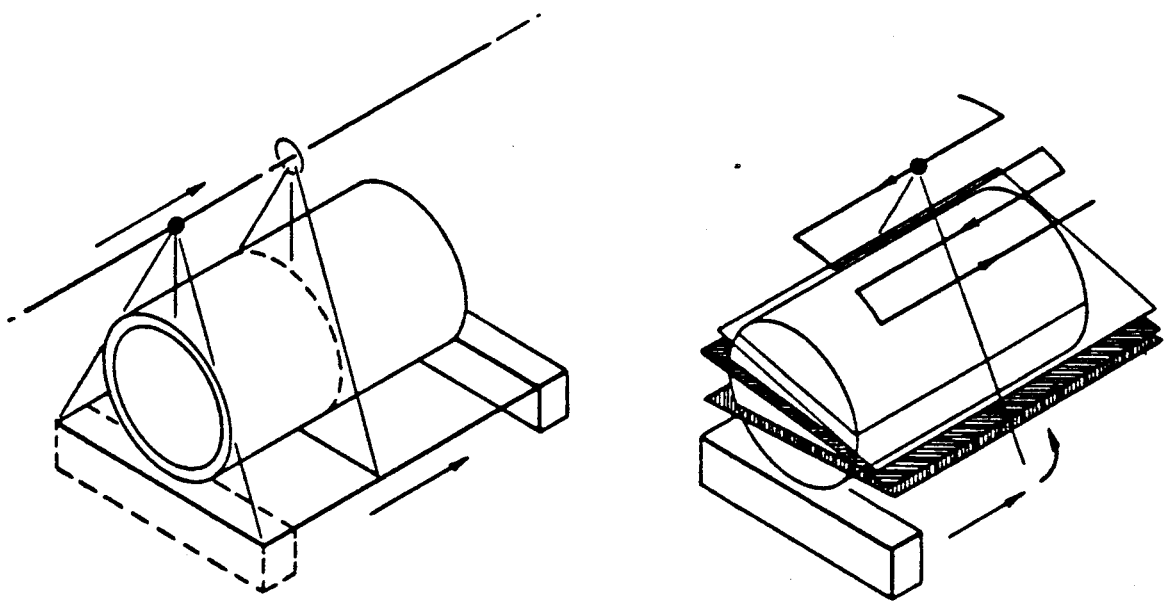
FIG. 7
FIG. 8

FIG. II

COMPUTERIZED TOMOGRAPHIC X-RAY SCANNER SYSTEM AND GANTRY ASSEMBLY

BRIEF DESCRIPTION OF THE INVENTION

This invention relates to a computerized tomographic x-ray scanner and gantry assembly and more particularly to a scanner gantry which can be moved to encircle objects to be scanned.

BACKGROUND OF THE INVENTION

The use of CT for imaging structures within the human body has revolutionized the diagnosis and care of patients. The high resolution images obtainable with currently available CT scanners combined with advanced computer image processing methods provides the capability for truly three-dimensional radiography. One of the most important roles played by a CT is its use in the emergency room of large hospitals. CT scanners have been placed in trucks so that the scanner may be transported to different hospitals or clinics for scanning. CT scanners have not been used in operating rooms due to their size, complexity and need for placing and moving the patient into and within the scanner.

CT scanners have found wide application in industry for nondestructive testing of objects such as turbine blades, rocket engines, composite structures, castings, welds and ceramic structures. The CT scanner is at a fixed location and the objects to be tested are moved to the scanner and rotated to provide the necessary scanning views. The use of scanners is limited to objects which can be moved and placed in the scanner.

Medium to large sized composites and metal structures such as aircraft, helicopters, etc., are subject to fatigue during use and must be inspected at frequent intervals. It is often necessary to dismantle such structures so that the parts can be moved to a fixed facility for inspection. In other instances, since it is not practical to disassemble the structure, CT x-ray scanning cannot be performed.

There is a need for a mobile CT scanner which can be used to image critical parts of large structures such as aircraft to detect damage, particularly in regions inaccessible to conventional inspection technology. There is a further need for such systems which permit inspection of the entire aircraft rapidly and at moderate cost. Other examples of industrial use of CT scanners are the inspection of wheels and landing assembly of aircraft parked at terminals, inspection of helicopter rotor blades and main rotor heads when the helicopter is parked at an air field. A mobile scanner can also be used for inspection of large forgings and castings in factories during fabrication, bridges and other structures.

OBJECTS AND SUMMARY OF THE INVENTION

It is an object of this invention to provide a gantry assembly for a computerized tomographic (CT) scanning system for industrial inspection.

It is another object of this invention to provide a mobile CT scanner system for industrial inspection.

It is a further object of this invention to provide a gantry assembly that allows the gantry to fit around objects to be inspected even if the ends of the object are not free.

It is a further object of this invention to provide a scanner gantry which can be manipulated to fit around objects to be inspected.

The foregoing and other objects of the present invention are achieved by a gantry which includes a support head with a C-shaped gantry rotatably mounted on the support head. An x-ray source is supported by the C-shaped gantry and projects an x-ray beam across said gantry. A detector array is mounted on the other side of the gantry for receiving the x-rays. The x-ray source and detector array may be moved around said gantry. The CT scanner also includes means for manipulating the gantry to cooperate with an object to be scanned.

BRIEF DESCRIPTION OF THE DRAWINGS

The foregoing and other objects of the invention will be more clearly understood when considered in connection with the accompanying drawings, of which:

FIG. 3 is a side elevational view of the gantry and support shown in FIG. 2.

FIG. 4 is a sectional view taken generally along the line 4—4 of FIG. 2.

FIG. 5 shows a CT scanner system including a gantry in accordance with this invention mounted for movement in a hanger and encircling the aircraft fuselage.

FIG. 6 shows the CT system of FIG. 5 inspecting an aircraft wing.

FIG. 7 shows the formation of a projecting image using the scanning system of the present invention.

FIG. 8 shows the system used for providing a transverse tomosynthesis scan.

DETAILED DESCRIPTION OF THE INVENTION

Figure 1:
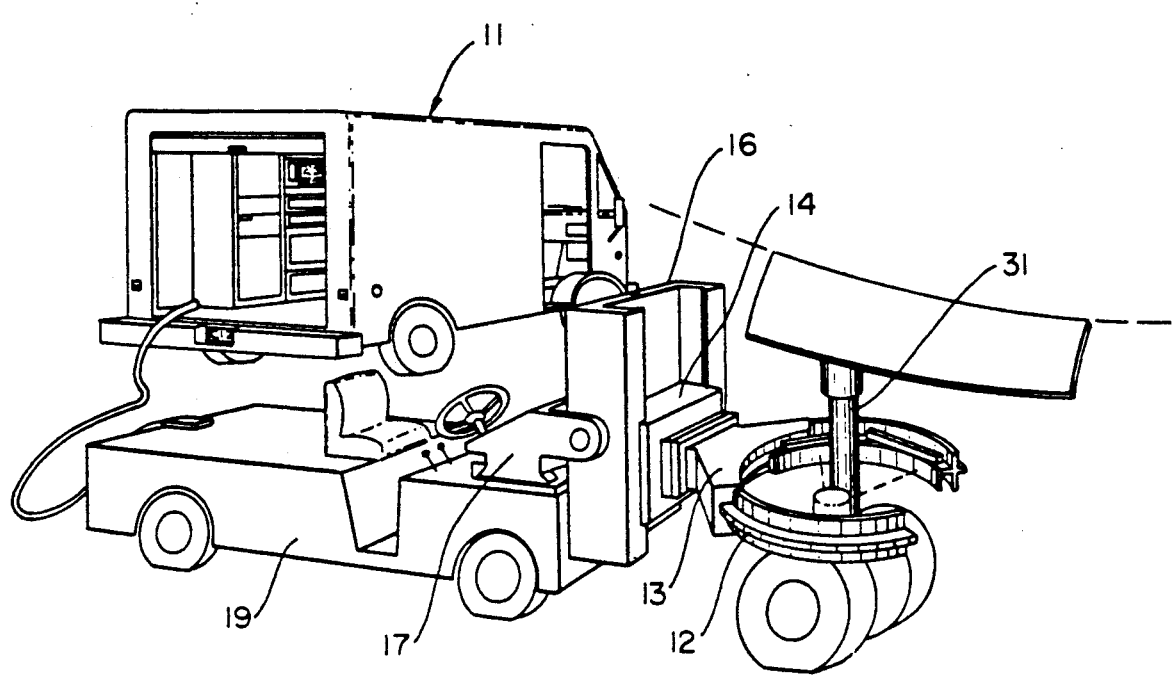
FIG. 1 is a schematic diagram showing a scanner system in accordance with one embodiment of the invention.

The scanner system shown in FIG. 1 consists of two principal parts. First, there is a mobile van 11, which contains the computer system and the imaging work station. The computer system includes an array processor for reconstruction, a general purpose processor, a file server and an imaging processing work station, all of which are well known in the art. A laser camera may be included for hard copy output. Software used for CT image reconstruction, storage, retrieval and application is also conventional. Although this part of the system is shown mounted in a van, it will become apparent that it may be mounted at a fixed location as, for example, in a hospital room and connected to the other part of the system by cables.

The second basic part of the system is a family of interchangeable, C-shaped gantries 12 which will differ in size to accommodate objects of various sizes. The gantry 12 is rotatably supported by a support head 13. The head 13 is rotatably mounted on the support 14 which travels in a guideway 16 for vertical movement. The guideway 16 may be tilted in the support 17, which is mounted on a lateral guideway 18 carried by a vehicle 19. Other gantry and support head manipulating means may be provided. For example, the gantry and support head can be mounted on a crane or other support.

Figure 2:
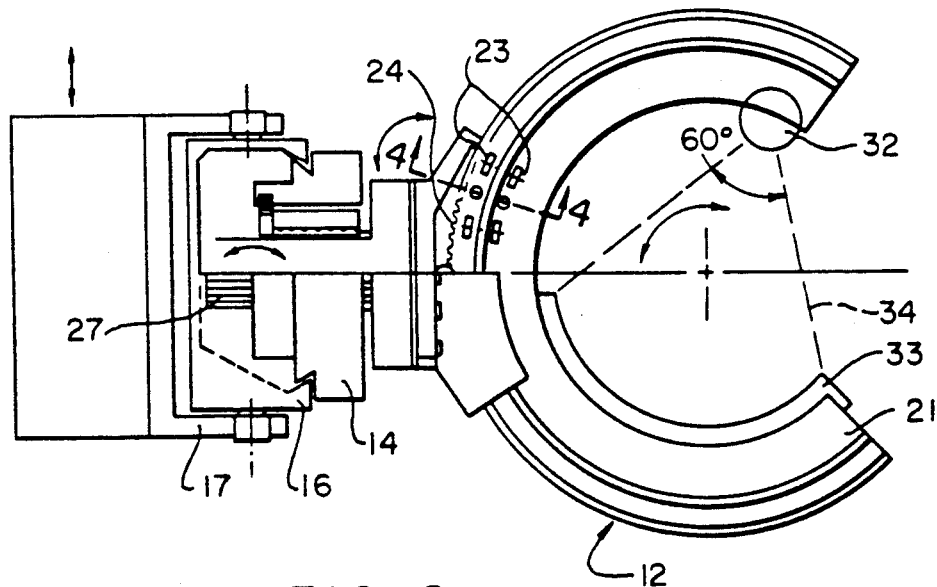
FIG. 2 is a bottom plan view of a gantry assembly and support head.

Referring to FIGS. 2-4, the gantry 12 includes a C-shaped casting or fabricated member 21 which, in cross-section, is T-shaped as shown at 22 and is supported within the head 13 by four pairs of spaced bearings 23 which securely support the C-shaped member while allowing it to rotate within the support head. The outer periphery of the C-shaped member 21 includes gears 24 engaged by and driven by a drive gear 26. The gear 26 is mounted in the head 13 and driven by a motor, not shown. Support head 13 is rotatably mounted on the support 14 and is rotated by motor driven gear means which engage the linear gear 27, which permits a second drive to move the head inwardly and outwardly from the support. The guideway 16 is tiltable by hydraulic means 28 secured between the supports 16 and 17.

Referring to FIG. 1, the vehicle can be moved to place the gantry about the object to be scanned. For example, the landing gear 31. Fine adjustment can then be made by rotating the head and moving it in and out so that the landing gear 31 is centered in the gantry for scanning.

Referring again to FIG. 2, the C-shaped gantry supports a conventional x-ray tube 32 on one side, and on the other side a detector array 33 which receives the fan-shaped beam 34. To scan an object, the gantry may be rotated or the x-ray source and detector array may be moved along the gantry, or both.

Referring again to FIG. 5, the gantry 12 is mounted on head 13 which is supported from a cross-member 36 which includes a traveling support member 37. The support member 37 can be moved longitudinally along the space support beams 38. The gantry is shown as being placed in cooperative relationship with the fuselage 39 of the aircraft.

In FIG. 6, the gantry is shown in position to scan the wing 40 of the aircraft. Thus, the C-shaped gantry permits scanning of objects without mechanical interference. As will be described, the open ends of the gantry can be closed, whereby to permit 360° rotation about an object being scanned. Not only is the support head 13 available for mounting a variety of sizes of gantries but, also, the gantries can be provided with a different type of x-ray sources depending upon the thickness and type of object to be imaged. During operation of the scanning system safety considerations will dictate precautions regarding access of personnel in the immediate inspection area during imaging. It may be necessary in certain instances to employ shielding.

The detector array used in the scanner is preferably based on photocrystal diode technology. The entire detector array is shielded from scattered radiation by a slit opening which accepts the primary fan beam and rejects stray radiation.

Figure 9:
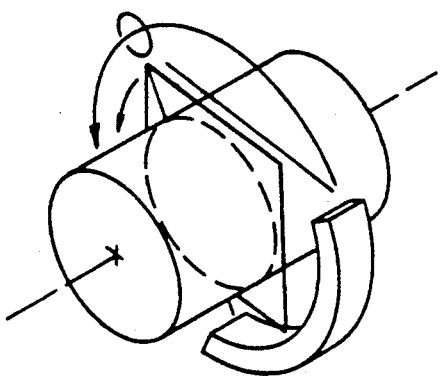
FIG. 9 shows the system configured to perform a CT scan.

Three types of scanning modes are possible with the scanner to image various portions of the scanned objects. These modes of scanning are schematically illustrated in FIGS. 7, 8 and 9. The line scanning mode in which the gantry is linearly moved produces a projection image using a principle similar to that employed in typical aircraft concourse x-ray scanners. In this case the object is stationary and the x-ray fan moves with linear motion across the object. Transverse tomographs are obtained by scanning projection images at multiple angles, FIG. 8. These data can then be reconstructed using a process called tomosynthesis to produce a tomographic image. In the CT mode, 180° of plane, FIG. 9. This involves rotation of the x-ray fan through an angle of 180° plus the source bandwidth, which gives a total of approximately 192° of scan.

Figure 10:
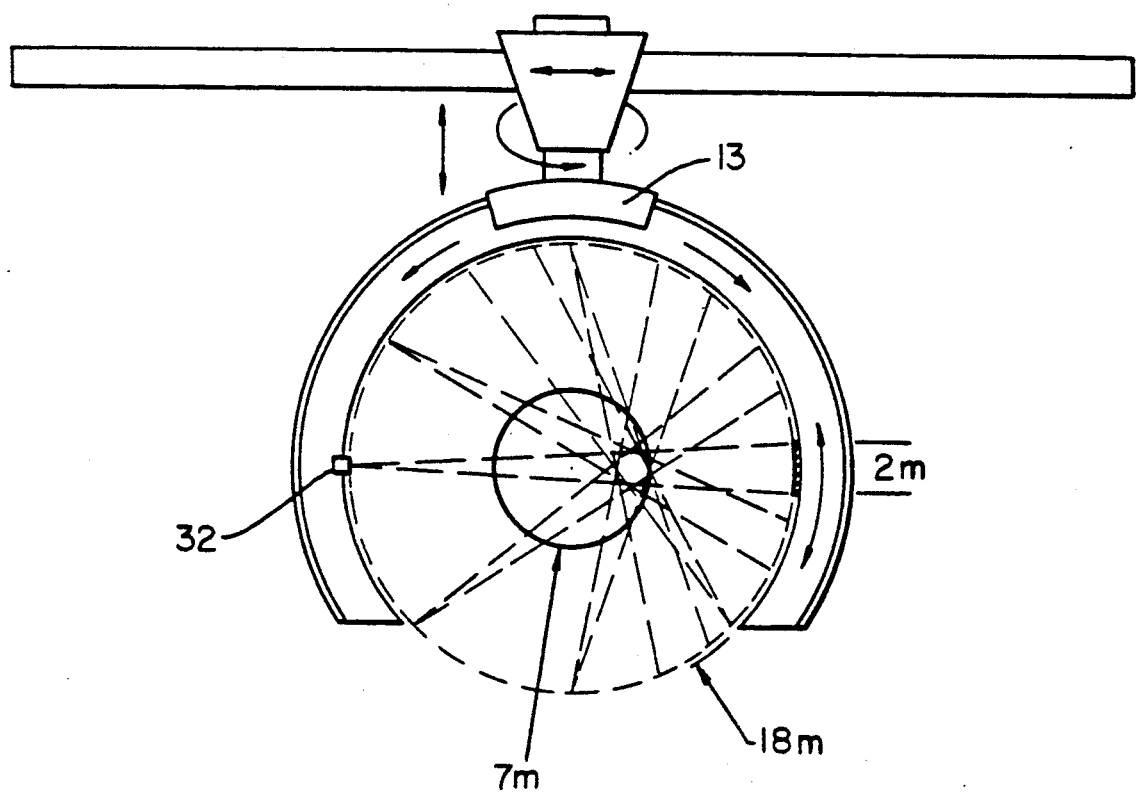
FIG. 10 is a schematic diagram illustrating the use of the scanner system for off-axis imaging of limited regions.

FIG. 10 shows a diagram of a method of scanning an off-axis region of interest. This scanning mode requires the source 32 or detectors 33 to rotate independently. If the region of interest can be positioned at the center of the gantry, dual motion of source and detector is avoided and the scan speed will be approximately four times faster. The modes are referred to in the literature as "limited region," "limited field of scanning" or "zoom CT". Dense objects outside the scanning region can sometimes generate artifacts within the region of interest. If this is the case, additional projection measurements can be obtained to provide corrections.

Figure 11:
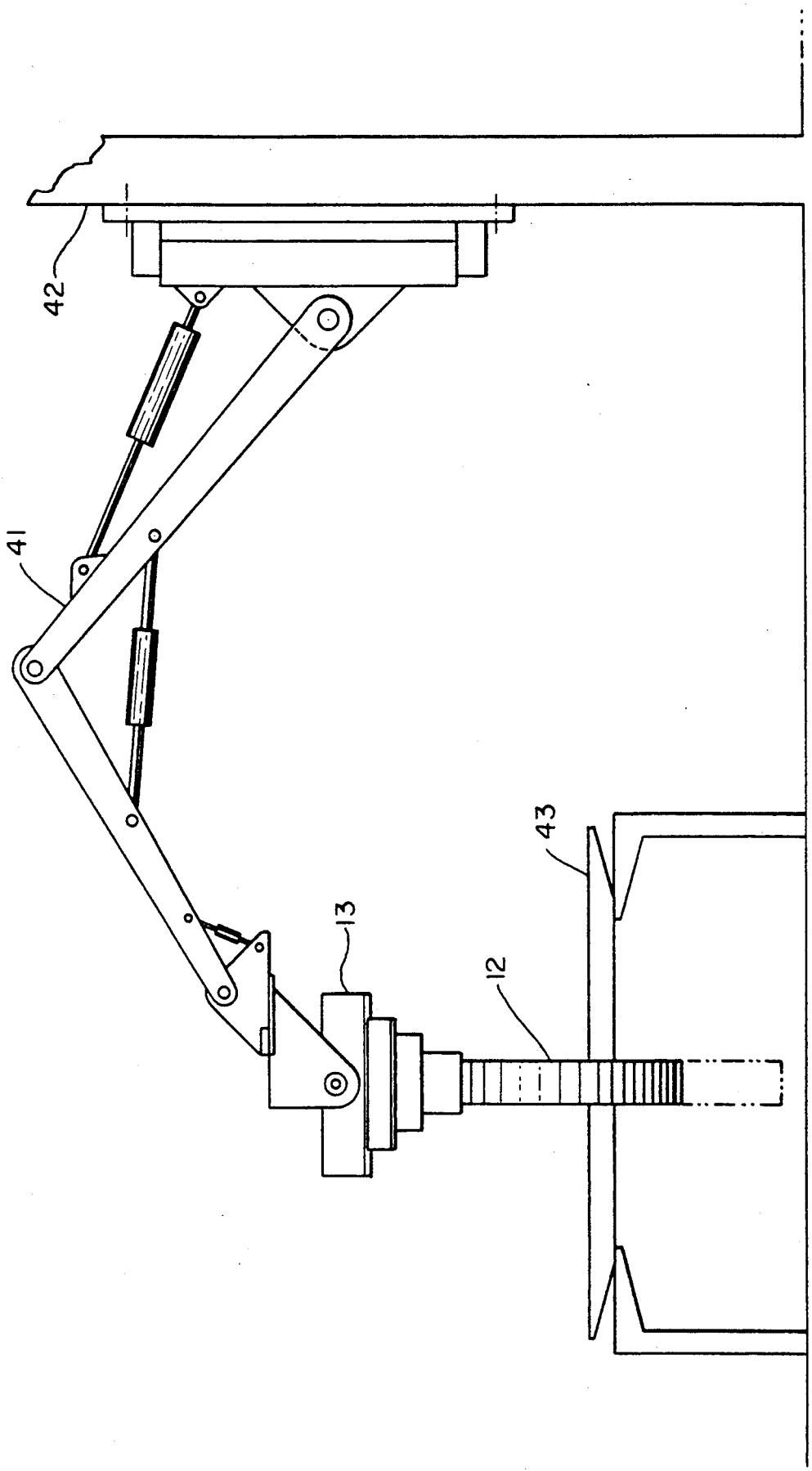
FIG. 11 shows the gantry of the invention mounted on the wall of a hospital room for manipulation into cooperative relationship with a patient table.

Referring to FIG. 11, the gantry 12 is mounted on a support head 13 attached to a hydraulically operated lever system 41 which positions the gantry. The gantry is shown supported from the wall 42 and moved into cooperation with a patient table 43.

Figure 12:
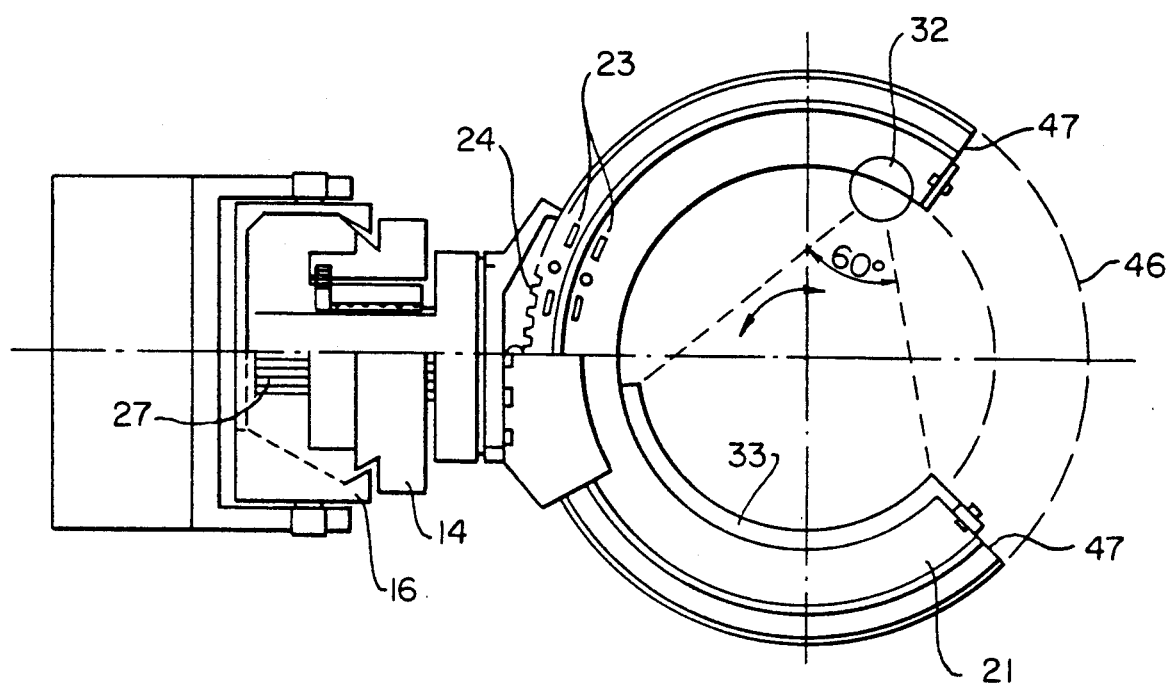
FIG. 12 shows a C-shaped gantry with the end closed to permit 360° of rotation of the gantry.

Reference was previously made to a 360° scan, for this purpose the open end of the C-shaped gantry is closed with a segment 46, FIG. 12, which is suitably secured to the ends 47 of the gantry. The gantry can then be rotated in the support head through 360° of rotation.

Thus, there has been provided a scanner in which the x-ray source and detector are moved into cooperative relationship with the object being scanned. The open end of the C-shaped support gantry passes over the object to place the object within the gantry where it is scanned by the x-ray source and scanner as they are rotated and moved.

What is claimed is:

1. A scanner assembly comprising
   a support head,
   a C-shaped gantry,
   means for supporting said gantry in said support head for rotating movement,
   an x-ray source mounted on one side of said gantry for independent movement with respect to a detector array along said gantry, said x-ray source projecting x-rays across said gantry, and
   a detector array mounted on the other side of a gantry for independent movement with respect to said x-ray source along said gantry, said detector array serving to receive said projected x-rays.

2. A scanner as in claim 1 including head support means for rotatably mounting said support head for rotation about an axis which is perpendicular to a rotational axis of said gantry.

3. A scanner as in claim 2 including means for mounting said head support for moving and positioning said support head whereby the gantry is placed in cooperative relationship with an object being scanned.

4. A scanner as in claim 3 in which said means for mounting said head support comprises a tiltable guideway.

* * * * *